United States Patent [19]

Kullas et al.

[11] Patent Number: 5,176,629
[45] Date of Patent: Jan. 5, 1993

[54] IRRIGATION SYSTEM FOR USE WITH ENDOSCOPIC PROCEDURE

[75] Inventors: Karen E. Kullas, Taunton, Mass.; Craig S. Nevers, Warwick, R.I.

[73] Assignee: C. R. Bard, Inc., Murray Hill, N.J.

[21] Appl. No.: 763,866

[22] Filed: Sep. 20, 1991

Related U.S. Application Data

[63] Continuation of Ser. No. 387,712, Jul. 31, 1989, abandoned.

[51] Int. Cl.$^5$ .............................................. A61B 17/32
[52] U.S. Cl. ........................................ 604/31; 604/30; 604/35; 604/118; 604/153
[58] Field of Search ...................... 604/27, 28, 30-35, 604/65, 67, 73, 118, 141, 147, 153, 246

[56] References Cited

U.S. PATENT DOCUMENTS

| | | |
|---|---|---|
| 3,429,313 | 2/1969 | Romanelli . |
| 4,117,843 | 10/1978 | Banko . |
| 4,261,360 | 4/1981 | Perez . |
| 4,561,431 | 12/1985 | Atkinson . |
| 4,604,089 | 8/1986 | Santangelo et al. ............... 604/35 |
| 4,634,430 | 1/1987 | Polaschegg ..................... 604/153 |
| 4,635,621 | 1/1987 | Atkinson . |
| 4,650,462 | 3/1987 | DeSainick et al. ............... 604/30 |
| 4,655,197 | 4/1987 | Atkinson . |
| 4,662,829 | 5/1987 | Nehring ........................ 604/153 |
| 4,781,687 | 11/1988 | Wall ............................ 604/151 |
| 4,820,265 | 4/1989 | DeSatnick et al. ............... 604/30 |
| 4,878,894 | 11/1989 | Sutter Jr. et al. ............... 604/32 |
| 4,902,277 | 2/1990 | Mathies et al. ................. 604/118 |
| 4,904,246 | 2/1990 | Atkinson ....................... 604/283 |
| 4,940,457 | 7/1990 | Olson .......................... 604/30 |

FOREIGN PATENT DOCUMENTS 2212066A 7/1989 United Kingdom .

OTHER PUBLICATIONS

Arthro-Automat 5002, F. M. Wiest KG manufacture brochure, (no date).
Elevated Position of the Irrigation Outflow During Arthroscopy: An Experimental Study (T. Dolk & B. G. Augustini) pp. 93-96, 1989.
Elevated Position of Suction Outflow During Arthroscopic Motorized Surgery: An Experimental Study (T. Dolk & B. G. Augustini) pp. 97-100, 1989.
Sales Brochure & Operator's Manual for 3M Arthroscopy Pump.
Sales Brochure for ARTHROVAC System sold by Snyder Laboratories/Zimmer Corp. Preliminary Sales Document "Greg Irrigation Monitor", AVEC Corp.

Primary Examiner—Stephen C. Pellegrino
Assistant Examiner—Ralph A. Lewis
Attorney, Agent, or Firm—Wolf, Greenfield & Sacks

[57] ABSTRACT

An irrigation system for irrigating and pressurizing a body cavity during an endoscopic procedure, such as during arthroscopy, includes a source of irrigation liquid, a pneumatically driven pump for pumping irrigation liquid from the source into the body cavity. The pump develops pulsatile flow and its operation is controlled by a pressure regulator that regulates the pressure of air applied to the pump. The system enables disablement of the pumping function of the pump while permitting gravity flow of irrigation liquid to the body cavity. The pump and associated tubing is inexpensive and adapted for one-time, disposable use.

33 Claims, 1 Drawing Sheet

IRRIGATION SYSTEM FOR USE WITH ENDOSCOPIC PROCEDURE This application is a continuation of application Ser. No. 07/387,712, filed Jul. 31, 1989, now abandoned.

FIELD OF THE INVENTION

This invention relates to irrigation systems for irrigating a body cavity during an endoscopic procedure, such as in an arthroscopic procedure.

BACKGROUND OF THE INVENTION

There are a variety of endoscopic procedures in which it may be desirable to irrigate a body cavity and in which the endoscope has been placed. For example, among the more common endoscopic procedures requiring irrigation is in the surgical treatment of the joints (knees, shoulders, elbows, wrists and ankles) by arthroscopic surgery. Arthroscopic surgery is far less invasive than open surgical procedures and has become widely accepted. A typical arthroscopic procedure lasts about 45 minutes to one hour as compared to three hours for an open surgical procedure. Arthroscopic surgery enables the surgeon to directly visualize the anatomy of the joint in a less invasive and reduced trauma procedure. Significantly less anesthesia is required in an arthroscopic procedure as compared to open surgery. The recovery from an arthroscopic procedure typically is much quicker than from open surgery.

Arthroscopy provides for the direct visualization of the interior of a joint through a fiber optic endoscope referred to as an arthroscope. The procedure enables the surgeon to diagnose and treat damage to the joint. For example, torn cartilage and debris can be located and removed using instruments specifically designed for arthroscopic surgery. The procedure involves the insertion of instruments into the joint through small incisions made in the region of the joint. When the arthroscopic procedure is diagnostic, typically two instruments are inserted into the joint. When the arthroscopic procedure is therapeutic, typically three or more instruments are inserted into the joint.

One instrument common to all arthroscopic procedures is an arthroscope which has light transmitting optical fibers by which the interior of the joint may be illuminated and observed through an eyepiece or by coupling the output optical fibers to a video camera and displaying the image on a video monitor. The endoscope typically has one or more conduits through which irrigation liquid may flow into or out of the joint. In a diagnostic procedure, the second instrument typically will be a probe with which the surgeon may probe the interior of the joint while observing the interior of the joint through the endoscope.

In either a diagnostic or a therapeutic arthroscopic procedure, it is necessary to cause irrigation liquid to enter the joint, under pressure. The irrigation liquid, usually saline solution, serves a number of purposes. The joint compartment normally is compressed and provides little room for the endoscope or the arthroscopic instruments. In order to provide room for the endoscope and the instruments and to enable the surgeon better to see all regions of the joint, the irrigation fluid is admitted to the interior of the joint under pressure to cause the joint to become distended. Once the irrigation solution has distended the joint, the surgeon has more room to manipulate the endoscope and the instruments as is necessary to perform the procedure. A further important effect of pressurizing the joint is to provide a tamponading effect, such as to minimize bleeding within the joint. The pressure, which is above the patient's blood pressure, tends to close off bleeding capillaries in tissue that may have been cut during the procedure. This is particularly important in situations where tourniquets are neither convenient nor effective, such as in the shoulders.

Distension of the joint is controlled by maintaining a desired level of pressure in the joint and by balancing the inflow and the outflow of irrigation solution. If the outflow exceeds the inflow, the joint will collapse and the surgeon must delay the procedure until distension is achieved. Distension may be maintained either by maintaining a continuous inflow and outflow at the joint or by intermittently closing both the inflow and the outflow while the surgeon works within the joint space and then, after the solution becomes murky, reestablishing inflow and outflow to flush the area with fresh solution. In either instance, controlling the flow rate is necessary to achieve sufficient distension without creating excessive intra-articular pressure. It is important to monitor the intra-articular pressure throughout the arthroscopic procedure and, to do so, surgeons frequently feel the outside of the joint to evaluate the bulges caused by the distension.

In a therapeutic arthroscopy, the amount of irrigation fluid flowing through the joint typically is greater than that when the procedure is merely diagnostic. The additional flow requirements result from the fact that the procedure will generate a considerable amount of debris which must be flushed from the joint not only to avoid post-operative complications from the procedure but also to facilitate the surgeons continued visualization of the interior of the Joint.

The most commonly used technique for irrigating the joint is by gravity flow of irrigation solution from an overhead supply. To that end, irrigation bags containing irrigation liquid are hung at a height of about 6 to 8 feet above the patient. A tube leading from the bags is connected to one of the ports of the arthroscope or to a separate irrigation cannula which will have been previously inserted into the joint. The tube typically is provided with a clamp which, when opened, enables the irrigation liquid to flow by gravity into the joint. A pulley system often is utilized so that the attending nurse can lower the bags and change them as they empty. By way of example, between about 3 to 15 liters of irrigation liquid typically are used on a knee arthroscopy although in some cases as many as 30 liters might be used. With the gravity system, the pressure of the irrigation liquid applied to the joint is dependent on the height of the bag containing the irrigation liquid.

The gravity system is awkward and presents a number of difficulties. For example, with some patients, particularly muscular patients, the gravity flow system does not distend the joint very effectively. Additional pressure is required. Many surgical facilities do not have sufficient height to distend the joint under such circumstances. Typically, this results in the necessity for an attending nurse to squeeze the irrigation bag continuously throughout the entire arthroscopy procedure. Also among the difficulties with the gravity system is that when a bag approaches being empty and must be changed, it must be pulled down from its elevated position. That reduces the fluid pressure in the joint and risks loss of distension.

As an alternate to the gravity system, it has been proposed to use pumps for irrigation. Such pumping systems typically have been cumbersome, complex and expensive. Two types of pumps have been used, a roller pump or a piston pump. Neither type of pump is adapted to convert from pumped flow to gravity flow. Thus, should such a pump fail during a procedure, it would be necessary to terminate the procedure and reconfigure the irrigation system to permit continued flow. Additionally, such devices typically are electrically powered which adds some measure of risk in view of the wet, conductive environment in which the device is used. Moreover, such pumps do not allow for continuous low pressure (gravity) flow. Continuous gravity flow often is considered important when it is desired to infuse cold irrigation solution without application of additional pressure such as to provide a tamponade effect by the cold temperature alone. Typically, such a procedure may be performed after the completion of the surgery.

It is among the general objects of the invention to provide an improved irrigation system for use in arthroscopy and other endoscopic procedures.

SUMMARY OF THE INVENTION

In accordance with the invention, the irrigation system uses a fluid powered, preferably pneumatically operated, diaphragm pulsatile pump. The pump is driven by a source of compressed air or nitrogen, as is available commonly in a hospital. The system includes a source of irrigation liquid contained in irrigation bags. The irrigation bags are connected by flexible tubing to the inlet side of the pump. The bags may be disposed about one to two feet above patient level. The pressurized gas also is connected to the driving side of the pump through a regulator that is preset to have a maximum pressure setting that will cause the pump to develop an output pressure of the order of 300 mm Hg, which corresponds to a 14 foot height above the patient of an irrigation bag. The outlet side of the pump is connected by tubing and a connector on its outlet end to an inflow cannula or the flow channel of the arthroscope through one of the ports of the arthroscope. The pressure and flow rate developed by the pump are controlled by adjusting the regulator. The regulator may be calibrated to read in height, corresponding to the range of approximately 6 to 14 feet of irrigation bag suspension above the patient. Should it be desired to change to a gravity system, that can be accomplished easily by adjusting the regulator to a lower pressure level at which the pump will cease operation. The construction of the pump is such that it will enable flow of irrigation liquid through the pump under the influence of the gravity head of the irrigation bag at a pressure level of as little of one foot of bag height. Should it be desired to shut off flow completely, that may be accomplished by closing a clamp on the pump outlet tubing or inlet tubing.

The pump provides a steady pulsatile flow. The pulsatile flow is desirable in that it provides for better irrigation in that it dislodges loose debris. Additionally, it causes loose but attached tissue, such as cartilage flaps or the like, to be more visible as they flap loosely or oscillate in the pulsatile flow. Should it be desired to shut off the pulsatile flow, that may be accomplished by shutting off the pump. The pump and associated tubing and irrigation bags are of inexpensive, simple construction and are disposable, thus lending themselves to one-time disposable use.

The pump is a two stroke pump that includes a housing divided into two compartments by a flexible, resilient element, such as an elastic diaphragm. The two chambers include a pumping chamber and a driving chamber. The pumping chamber has inlet and outlet ports which are connected, respectively, to the irrigation liquid supply and the conduit leading to the irrigation cannula or the irrigation channel in the arthroscope. A check valve arrangement is provided in the system to assure flow only in a direction from the inlet to the outlet of the pump. The driving chamber also is provided with an inlet port and an outlet port, the inlet port of the driving chamber being connectable to a source of gas under pressure. The outlet, when open, is exhausted to the atmosphere. The device is arranged such that an elastic diaphragm normally closes the outlet port. The pumping action is effected by applying pneumatic pressure at the inlet to the driving chamber. The increased pressure in the pneumatic chamber causes flexure and expansion of the portion of the diaphragm which surrounds, but does not seal the outlet port. Expansion of the diaphragm to the pumping chamber in a first stroke causes a volume of fluid to be ejected out of a pumping chamber. The ejection continues until the expansion of the diaphragm overcomes the bias of the diaphragm against the outlet. At that point, the diaphragm abruptly snaps to a configuration opening the outlet port thereby exhaust venting the driving chamber to atmosphere. Once the outlet is open the pressure across the diaphragm equalizes which enables the diaphragm to return in a second stroke to its normal position closing the outlet port. During the second stroke, the volume of the pumping chamber is reexpanded which ingests an additional volume of irrigation liquid into the pumping chamber in readiness for the next oscillation.

It is among the general objects of the invention to provide a simple, inexpensive, disposable system for endoscopic irrigation.

Another object of the invention is to provide an irrigation system of the type described which enables forcefully pressured as well as gravity flow of irrigation liquid.

A further object of the invention is to provide an irrigation system for irrigating a body cavity in an endoscopic procedure that includes a fluid powered pumping system.

A further object of the invention is to provide a system of the type described in which the pump generates a pulsatile flow in which the system may automatically default to or be controlled to operate, alternately, in a gravity mode.

Another object of the invention is to provide a system of the type described which is free of electrical connections, wiring or appliances.

A further object of the invention is to provide a system of the type described which is pneumatically operated.

A further object of the invention is to provide a system of the type described in which the pump is constructed to shut off automatically when a predetermined pressure is reached and to restart immediately when the pressure drops below the predetermined pressure.

Still another object of the invention is to provide a system of the type described that is quick to set up, requires very few connections and is easy to use.

DESCRIPTION OF THE DRAWINGS

The foregoing and other objects and advantages of the invention will be appreciated more fully from the following further description thereof, with reference to the accompanying drawings wherein.

DESCRIPTION OF THE ILLUSTRATIVE EMBODIMENT

Figure 1:
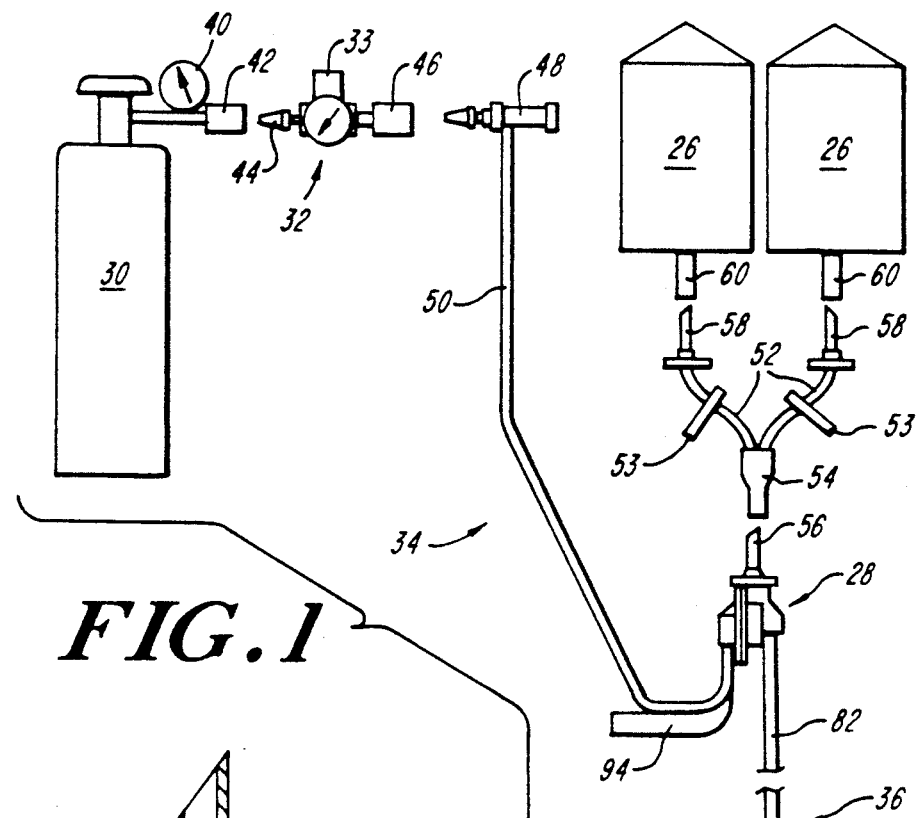
FIG. 1 is a somewhat diagrammatic illustration of the system set up to perform a therapeutic arthroscopic procedure on a knee (out of scale)

FIG. 1 illustrates, somewhat diagrammatically (and out of scale), the system as set up to perform a therapeutic arthroscopy on a patient's knee 10. In the illustration, the patient's knee will have at least three members inserted into the knee joint including the arthroscope 12, a flow cannula 14 and a surgical instrument, indicated generally by the reference character 16.

The arthroscope 12 carries optical fibers arranged to deliver light from a suitable source (not shown) into the interior of the knee joint as well as to permit viewing by the surgeon into the knee joint through the eyepiece 18. Alternately, the arthroscope 12 may be coupled to a video camera to display the image of the interior of the joint on a video monitor. The arthroscope 12 also typically will have one flow channel leading to ports 20, 22 which may be connected to the appropriate tubing. The ports 20, 22 may include stopcocks to open or close the flow channel as desired. Depending on the manner in which the surgeon wishes to set up the apparatus, the ports 20, 22, may be used as inflow channels into the joint or outflow channels to direct fluid from the joint or in a different mode one port may be used for inflow and the other, alternately, for outflow.

The flow cannula 14 also is provided with a stopcock 24 by which flow though the cannula 14 may be controlled between on and off positions. The flow cannula 14 is used to provide additional flow capacity to or from the joint in addition to the flow capacity provided by the flow channel in the arthroscope 12. Typically, such additional flow capacity will be required when performing a therapeutic procedure as compared to a diagnostic procedure in which less flow capacity is required. Again, depending on the manner in which the surgeon wishes to set up the flow pattern, the flow cannula may be used as an inflow or an outflow member, it being illustrated as in inflow member.

The surgical instrument 16 may take any of a variety of forms adapted to cut, scrape, shave or the like, as will be appreciated by those familiar with the art. Typically, such surgical instruments adapted for use in arthroscopy also incorporate suction capability by which liquid and debris is ingested and withdrawn from the interior of the joint. Thus, the surgical instruments often also serves as an outflow cannula as well as performing a surgical function on tissue within the joint. In the illustrative embodiment, it will be appreciated that the inflow of irrigation liquid is through the flow cannula 14 and the outflow of irrigation liquid and debris will be from one or more of the surgical instruments 16 or flow channel through the arthroscope 12.

The irrigation system, as illustrated in FIG. 1 includes a supply of irrigation liquid which may be in the form of one or more flexible bags 26 containing the liquid. The system also includes a fluid driven pump 28, the driving fluid preferably being a gas such as air or nitrogen. The driving gas, under pressure, is supplied from a source, indicated diagrammatically at 30 and may be in the form of bottled gas or may be conveniently from a convenient hospital wall supply. The gas is supplied through a regulator 32 and a tubing set 34 to the pump 28. The liquid outflow side of the pump 28 is connected through a tubing set 36 and a connector tube 38 to the inlet to flow cannula 14.

The gas source 30 is provided with a pressure gauge 40 and a connector 42 which mates with a connector 44 on the pressure regulator 32. The pressure regulator 32 includes another connector 46 which mates with a connector 48 on the end of a flexible tube 50 of the tubing set 34. The other end of the tube 50 is connected to the pump 28 to deliver gas under pressure to the pump 28 to drive the pump in the manner described below.

The pump 28 is connected to the irrigation bags receptive fitting 60 by tubing 52 or directly by spike connector 56. One end of the tubing has an adapter 54 to receive a spike connector 56 of the pump 28. The other end of the tubing 52 includes a spike connector 58 that is insertable into a receptive fitting 60 on each irrigation bag 26.

Figure 2:
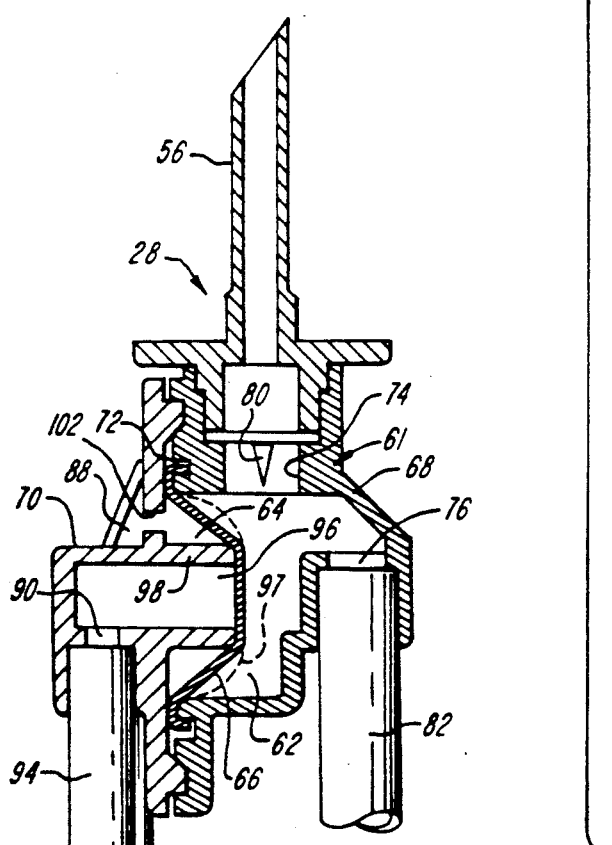
FIG. 2 is a sectional illustration of the pneumatically driven pump in the illustrative embodiment of the invention.

The pump 28 preferably is of the type described in U.S. Pat. No. 4,662,829 dated May 5, 1987 and entitled Pulsatile Pump, the disclosure of which is incorporated herein by reference. FIG. 2 illustrates, somewhat diagrammatically, a configuration of such a pump. The pump includes a housing 61 which may be molded, in components, from appropriate plastic materials. The interior of the housing is divided into a variable volume pumping chamber 62 and a driving chamber 64, the chamber 62, 64 being defined in part and separated by a flexible, resilient member 66, such as an elastic diaphragm. The housing 61 may be formed in two sections 68, 70. The flexible resilient member 66 preferably is captured between the housing section 68, 70 when the device is assembled. The periphery of the diaphragm may be provided with an enlarged rim 72 which can be received in a receptive groove formed in one or both of the sections 68, 70 to cooperatively grip the rim 72. The housing section 68, 70 and the periphery of the flexible resilient member 66 are sealed to assure hermetic isolation between the chamber 62, 64 as well as a complete seal to the atmosphere.

The housing 61 includes a fluid inlet 74 and a fluid outlet 76 leading to and from the pumping chamber 62. The inlet is connected through spike connector 56 to the irrigation bags 26 by the tubing arrangement 52. The device also includes means for maintaining unidirectional flow along the flow path defined by the inlet 74, pumping chamber 62 and outlet 76 and, to that end, a check valve 80, such as a duck bill type valve, is placed along the flow path, preferably adjacent the inlet 74.

The outlet 76 of the housing 61 is in communication with a pump outflow tube 82 (which is an inflow tube with respect to the knee joint) that forms part of the tubing set 36. The tube connector 38 is provided with an adjustable clamp 84 which can be set to partially or completely obstruct the tube connector 38.

The pumping action is effective by oscillations of the elastic diaphragm 66. The device includes a two stroke mode of operation, including an ejection stroke and a filling stroke. In the ejection stroke, diaphragm 66 is caused to flex to decrease the volume of the pumping chamber 62, applying pressure to the fluid in the chamber 62. During the ejection stroke, fluid is caused to flow from the pumping chamber 62 into the tubing 82, through the tube connector 38 and into the flow cannula 14. Reverse flow is prevented by the check valve 80. As described below, the ejection stroke is terminated abruptly in a manner to enable the elastic diaphragm 66 to return to its starting position in which the volume of pumping chamber 62 reexpands to its original volume. The reexpansion of the member 66 defines the filling stroke and causes fluid to be drawn from the irrigation bags 26 through the tubing 52 and check valve 80 to the pumping chamber 62 in readiness for the next pumping stroke.

The flexible, resilient member 66 is constructed and mounted in the housing 61 so that it can oscillate under the influence of positive pneumatic pressure applied to the driving chamber 64. To that end, the device includes an air inlet passage 88 and an air outlet passage 90. The inlet passage 88 is connected to a source of air or other appropriate gas under pressure by the air inlet tube 50 which is in communication with the air inlet passage 88. Exhaust air from the air outlet passage 90 may be communicated from the driving chamber by an exhaust tube 94. The air exhaust passage 90 leads from an exhaust port 96 which is located in registry with the center of the elastic element 66. Exhaust port 96 is arranged to communicate with the driving chamber 64. The diaphragm 66 is normally biased to the exhaust port 96 so as to seal off the exhaust port from the driving chamber 64. The diaphragm is biased by its elasticity and by providing a bearing member such as an upstanding wall 98 which surrounds the exhaust port over which the elastic diaphragm 66 is stretched. In this configuration of the device, the height and location of the wall 98 is selected with respect to the manner in which the peripheral rim 72 of the diaphragm 66 is held in place. In the embodiment shown, the elastic diaphragm 66 is stretched into a dome shape and is maintained under elastic tension which biases the diaphragm 66 toward the exhaust port 96 to close the port 96. Thus, the driving chamber 64 may be considered as somewhat annularly shaped, being bounded by the wall 98, the surface of the elastic diaphragm 66 and portions of the housing 70. The air inlet passage 88 communicates with the driving chamber 64 at an air inlet port 102 which opens through a wall in the housing section 70.

In operating the pump, it first must be primed so that liquid to be pumped completely fills the flow path from the reservoir bags 26 to the cannula 14. Priming is accomplished easily by opening all the clamps and stopcock 24 and allowing the liquid to flow by gravity or under light pressure through the system. In the ejection stroke of the cycle, pneumatic pressure is applied in air inlet tube 102. As the pressure builds up within the driving chamber 64 the elastic diaphragm expands to form a domed annular configuration, suggested in exaggerated phantom at 97 in FIG. 2, while maintaining its seal against the end of the annular wall 98. The pressure built up within the driving chamber 64 is applied, through the diaphragm, to the fluid in the pumping chamber 62 thereby ejecting fluid through the outlet 76. The volume of fluid pumped in the ejection stroke is equal to the difference in volume in the driving chamber from its relaxed position to its position of maximum expansion.

The ejection stroke continues as long as the diaphragm remains biased in its sealed relation against the exhaust port 96. The biasing force is created by the inherent elasticity of the diaphragm in the manner in which it is stretched over the rim of the wall 98 which surrounds and defines the exhaust port 96. The central portion of the diaphragm which makes the seal against the rim of the wall 98 maintains that seal until the remaining portion of the diaphragm 66 has been flexed and expanded to a point in which the opening force applied to the central portion of the diaphragm by the expanding peripheral portions of the diaphragm exceeds the biasing force. The central portion of the diaphragm is maintained in seated, sealed relation against the rim of the wall 98 not only under the influence of the bias of the elastic diaphragm but also under the influence of a pulse of increased pressure applied to the fluid in the pumping chamber. Thus, as the diaphragm expands into the annular dome-shaped configuration, the pressure pulse applied to the liquid in the pumping chamber forces the central portion of the diaphragm more firmly into seated engagement on the rim of the wall 98. That additional pressure enables the diaphragm to expand to an annular domed configuration in which the central portion of the diaphragm remains depressed in a dimpled configuration with respect to the annular expanding portion of the diaphragm during a portion of the ejection stroke. In this regard, it should be noticed that the impedance on the outlet side of the pump also has an affect on the timing of the unseating of the diaphragm from the air outlet port. The impedance should be great enough to allow sufficient pressure to build up within the pumping chamber so as to maintain the central portion of the diaphragm in sealing engagement on the outlet port for a time sufficient to enable a desired volume of liquid to be pumped during the ejection stroke. As the ejection stroke nears completion, the stretched diaphragm abruptly unseats the central portion of the diaphragm from its sealing engagement with the rim of the wall 98.

At the moment that the sealed, central portion of the diaphragm abruptly unseats from the rim of the wall 98, the elastic diaphragm immediately assumes a more uniform dome shape under the influence of the equalization of the internal elastic forces in the diaphragm. The internal elastic forces within the diaphragm 66 cause the diaphragm to contract which draws the diaphragm down into sealing engagement with the rim of the wall 98.

During the elastic contraction of the diaphragm the air which was in the driving chamber 64 is exhausted immediately and rapidly through exhaust port 98, 96, air outlet passage 90 and exhaust tube 94. Immediate and rapid exhaust from the driving chamber 64 is assured by providing substantially larger outlet passages than those associated with the air inlet. Thus, outlet port 96, air outlet passage 90 and exhaust tube 94 are arranged so as to present a minimum of back pressure which might impede rapid exhaust of air from the driving chamber.

In order to assure that the diaphragm will collapse rapidly, it is important that the impedance in the air outlet line is substantially less than in the air inlet. This may be accomplished by selectively proportioning the flow areas of the air inlet and air outlet.

Operation of the system is controlled by pressure regulator 32. Regulator 32 is adjustable, as by a knob control 33, to supply air under pressure to the pump 28. The regulator, which may be any of a number of commercially available regulators, is preset in relation to the operating characteristics of the pump 28 so as to have a maximum outlet pressure that will result in a maximum fluid pressure at the outlet of the pump of the order of 300 mm Hg. Such a pressure corresponds to an approximate maximum height (about 14 feet above the patient) to which the irrigation bags are raised at a gravity mode. The regulator may be adjusted to provide lower air pressures to the pump 28 which will result in correspondingly lower outlet pressures, flow rates and pulse rates of the irrigation liquid. The setting for the regulator 32 is controlled in conjunction with management of the rate of irrigation liquid outflow from the joint. Such outflow may be controlled by the stopcocks 20, 22 or by appropriate controls associated with the suction side of the surgical instrument 16. Thus, in order to maintain the desired degree of joint distension and the desired degree of irrigation liquid outflow, the pressure regulator 32 may be adjusted to drive the pump 28 to a desired corresponding output pressure. In operation, with the pressure regulator set to a predetermined level, the pump will automatically stop operating once the corresponding liquid pressure has been reached. Should the pressure of the liquid drop, for example, from an increase in the outflow of liquid from the joint, the pump restarts automatically and immediately to maintain the selected pressure level. In this manner, the system is very effective in maintaining the desired degree of pressure and joint distension. It will be appreciated that the various parameters may be adjusted as desired to suit the requirements of the particular procedure being performed.

Among the advantages of the system is that the pump provides a controllable pulsatile flow. The pulsatile flow is desirable because it tends to dislodge and trap debris and enhances the cleansing action of the irrigation liquid. Additionally, during diagnosis and evaluation, the pulsating action of the liquid tends to highlight loose tissue or cartilage segments, such as cartilage flaps, by enhancing their movement and rendering them more visible. Should it be desired to stop the pulsatile flow, for example, to make it easier to grasp and surgically repair a particular portion of the joint, that may be accomplished in several ways. If it is desired simply to convert the system to a gravity mode of operation in which the pulsatile flow stops while gravity irrigation continues, that may be accomplished by adjusting the regulator to a reduced pneumatic pressure, below the threshold necessary to raise the diaphragm 66 from the upper end of the annular wall 98. While maintaining clamps 53 and 84 open, as well as stopcock 24, irrigation liquid will continue to flow through the system and through the one-way check valve 80. In this regard, the check valve 80 should be selected so as to permit flow of irrigation liquid under a gravity head of the order of one foot. Alternately, should it be desired to terminate all flow and pulsation during a particular portion of the procedure, that may be accomplished simply by closing the clamp 84 and/or the stopcock 24. Distension of the joint can be maintained by closing all outflow passages, thus trapping the distending volume of irrigation liquid in the joint.

The gauge on the pressure regulator may be calibrated in direct pressure readings as well as in corresponding equivalent irrigation bag height in order to facilitate correlation of the regulator settings with terminology familiar to those who have used gravity drainage systems.

From the foregoing, it will be appreciated that the device operates free of any electrically connections or wirings. It is quick and easy to set up with very few connections. The entire system of irrigation bag, tubing and pump is inexpensive and lends itself to one-time disposable use. It provides pulsatile as well as gravity flow capability and is easily switched between those modes of operation.

It should be understood that although the invention has been described in connection with an arthroscopy procedure on a knee, it should be understood that is equally usable with other non-arthroscopic procedures. For example, the invention may be used in irrigation of the bladder or other body cavities in conjunction with endoscopic procedures.

It should be understood that the foregoing description of the invention is intended merely to be illustrative and that other embodiments and modifications may be apparent to those skilled in the art without departing from its spirit.

Having thus described the invention, what I desire to claim and secure by Letters Patent is:

1. An irrigation system for irrigating, and automatically maintaining a constant fluid pressure in, a body cavity during an endoscopic procedure comprising:
    a source of irrigation liquid;
    a first, inflow conduit for delivering irrigation liquid into the body cavity;
    a pressurized fluid driven pump means for pumping liquid from the source to the inflow conduit at a variable fluid flow rate, said pump having an output and constructed to produce an average fluid pressure at the pump output which average pressure is proportional to the pressure of fluid that drives the pump;
    pressure regulating means for regulating the pressure of the driving fluid to a value which is substantially constant around a selected value;
    a second conduit connecting the source of irrigation liquid with the pump;
    a third, outflow conduit adapted to direct flow of irrigation liquid out of the body cavity; and
    means for regulating flow of irrigation liquid out of the body cavity so that fluid pressure develops in the cavity.

2. An irrigation system as defined in claim 1 wherein the pump means is constructed to develop a pulsatile output.

3. An irrigation system as defined in claims 1 or 2 wherein the pump means is pneumatically driven.

4. An irrigation system as defined in claim 3 wherein the pump means and second conduit are comprised of a polymeric material.

5. An irrigation system as defined in claims 1 or 2 wherein the pump means is constructed and arranged to enable gravity flow of liquid through the pump means when the pump means is not operating.

6. An irrigation system as defined in claim 5 wherein said gravity flow is enabled by means comprising:
    the pump means having a movable pump element separating the pump means into a pumping chamber and a driving chamber;
    the pump means being so constructed and arranged that the movable pump element does not obstruct flow of liquid through the pumping chamber;
    said first and second conduits being connected to the pumping chamber;

one-way valve means associated with a flow path extending through said conduits and said pumping chamber for establishing one-way flow toward the body cavity;

whereby upon disablement of the pump means, irrigation liquid may flow by gravity through the system to the body cavity.

7. An irrigation system as defined in claim 6 wherein the movable pump element comprises a diaphragm adapted to oscillate within the pump means.

8. An irrigation system as defined in claim 7 wherein the pump means and second conduit are comprised of a polymeric material.

9. An irrigation system as defined in claim 7 further comprising:

said pump means being constructed and arranged to shut off automatically when a predetermined output pressure level has been reached and to restart immediately when the output pressure drops below said predetermined level.

10. An irrigation system as defined in claim 6 wherein the system is free of electrical devices.

11. An irrigation system as defined in claim 6 wherein the pump means and second conduit are comprised of a polymeric material.

12. An irrigation system as defined in claim 6 further comprising:

said pump means being constructed and arranged to shut off automatically when a predetermined output pressure level has been reached and to restart immediately when the output pressure drops below said predetermined level.

13. An irrigation system as defined in claim 5 wherein the pump means and second conduit are comprised of a polymeric material.

14. An irrigation system as defined in claim 5 further comprising:

said pump means being constructed and arranged to shut off automatically when a predetermined output pressure level has been reached and to restart immediately when the output pressure drops below said predetermined level.

15. An irrigation system as defined in claims 1 or 2 wherein the system is free of electrical devices.

16. An irrigation system as defined in claims 1 or 2 further comprising an adjustable restrictor clamp associated with the first conduit.

17. An irrigation system as defined in claim 16 further comprising:

said pump means being constructed and arranged to shut off automatically when a predetermined output pressure level has been reached and to restart immediately when the output pressure drops below said predetermined level.

18. An irrigation system as defined in claim 1 wherein the pressure regulator has a fixed maximum output limit.

19. An irrigation system as defined in claim 18 wherein said maximum limit corresponds, in conjunction with the pump means, to a pump output pressure of about 300 mm Hg.

20. An irrigation system as defined in claims 1, 2, 18 or 19 wherein the pump means and second conduit are comprised of a polymeric material.

21. An irrigation system for irrigating a body cavity during an endoscopic procedure as defined in any of claims 1, 2, 18 or 19 further comprising:

said pump means being constructed and arranged to shut off automatically when a predetermined output pressure level has been reached and to restart immediately when the output pressure drops below said predetermined level.

22. An apparatus for use in an irrigation system for irrigating a body cavity with an irrigation liquid from an irrigation source and maintaining a constant liquid pressure in the body cavity during an endoscopic procedure, the system having means for restricting irrigation liquid from flowing out of the body cavity to cause liquid pressure to build up inside of the body cavity, the apparatus comprising:

a first inflow conduit for delivering irrigation liquid into the body cavity;

a pressurized fluid driven pump means for pumping liquid from the irrigation source to the inflow conduit at a variable flow rate, said pump having an output connected to the first inflow conduit and constructed to produce an average fluid pressure at the pump output which average fluid pressure is substantially proportional to the pressure of fluid that drives the pump; and pressure regulating means for regulating the pressure of the driving fluid to a value which is substantially constant around a selected value.

23. An apparatus as defined in claim 22 wherein the pump is adapted to develop a pulsatile output.

24. An apparatus as defined in claims 22 or 23 wherein the pump is constructed and arranged to enable gravity flow of liquid through the pump when the pump is not operating.

25. An apparatus as defined in claim 24 wherein the apparatus is comprised of a polymeric material.

26. An apparatus as defined in claim 24 wherein said gravity flow is enabled by means comprising the pump having a movable pump element separating the pump into a pumping chamber and a driving chamber;

the pump being so constructed and arranged that the pumping element does not obstruct flow of liquid through the pumping chamber;

said first and second conduits being connected to the pump chamber;

one-way valve means associated with the flow path extending through said conduits and said pumping chamber for establishing one-way flow toward the body cavity;

whereby upon disablement of the pump, irrigation liquid may flow by gravity through the system to the body cavity.

27. An apparatus as defined in claim 26 wherein the apparatus is comprised of a polymeric material.

28. An apparatus as defined in claim 26 wherein the movable pump element comprises a diaphragm adapted to oscillate within the pump.

29. An apparatus as defined in claim 28 wherein the apparatus is comprised of a polymeric material.

30. An apparatus as defined in claim 22 wherein the pump is pneumatically driven.

31. An apparatus as defined in any of claims 22-30 wherein the apparatus is comprised of a polymeric material.

32. An apparatus as defined in claim 22 further comprising:

regulating means connected between the pump and a source of pressurized driving fluid for regulating the pressure of the driving fluid so that the liquid pressure in the body cavity can be controlled by adjusting the regulating means.

33. A method for irrigating a body cavity during an endoscopic procedure comprising the steps of:
providing a source of irrigation liquid;
providing a first inflow conduit for delivering irrigation liquid into the body cavity;
pumping, by a pressurized fluid driven pump, irrigation liquid from the source to the inflow conduit at a variable flow rate, said pump having an output connected to the first inflow conduit and constructed to produce an average fluid pressure at the pump output which average fluid pressure is substantially proportional to the pressure of fluid that drives the pump;
restricting the flow of irrigation liquid out of the body cavity so that fluid pressure builds up in the body cavity; and
regulating the pressure of fluid that drives the pump so that the driving fluid has an average pressure value which is substantially constant around a selected value.

* * * * *